United States Patent [19]

Kagara et al.

[11] Patent Number: 5,543,525
[45] Date of Patent: Aug. 6, 1996

[54] PROCESS FOR PRODUCING PYRROLIDINE DERIVATIVE AND SALT THEREOF

[75] Inventors: Kohji Kagara, Minoo; Shunsuke Goto, Osaka; Satoshi Yonishi, Nishinomiya; Muneharu Ikushima, Osaka; Yukihisa Baba, Amagasaki; Haruo Horiai, Nishiomiya, all of Japan

[73] Assignee: Fujisawa Pharmaceutical Co., Ltd., Osaka, Japan

[21] Appl. No.: 360,679

[22] PCT Filed: Jun. 29, 1993

[86] PCT No.: PCT/JP93/00886

§ 371 Date: Dec. 30, 1994

§ 102(e) Date: Dec. 30, 1994

[87] PCT Pub. No.: WO94/01400

PCT Pub. Date: Jan. 20, 1994

[30] Foreign Application Priority Data

Jul. 2, 1992 [JP] Japan ................................. 4-175200

[51] Int. Cl.$^6$ .................................................. C07D 401/06
[52] U.S. Cl. .................. 546/279.1; 548/518; 548/314.7; 548/364.1; 544/333; 544/405; 544/238; 544/180; 544/255; 546/278.4
[58] Field of Search ............................ 546/281; 514/343; 548/518, 314.7, 364.1; 544/333, 405, 238, 180, 255

[56] References Cited

U.S. PATENT DOCUMENTS 4,876,262 10/1989 Oinuma et al. .................... 546/281

OTHER PUBLICATIONS

Yadav et al. CA 119:27898, 1993. Takuma et al. CA 115:255891, 1991.
Main et al. CA 117: 233411, 1992. Beaulieu et al. CA 115: 9267, 1991.
Zjawiony et al. CA 114: 185330, 1991. Moiseenkov et al. CA 111: 174466, 1989.

*Primary Examiner*—Jane Fan
*Attorney, Agent, or Firm*—Oblon, Spivak, McClelland, Maier, & Neustadt, P.C.

[57] ABSTRACT

A process for producing a compound of the general formula:

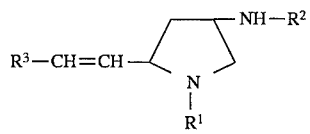

wherein
$R^1$ is heterocyclic(lower)alkyl,
$R^2$ is acyl, and
$R^3$ is carboxy(lower)alkyl or protected carboxy (lower) alkyl, which is useful as a medicament or a salt thereof.

1 Claim, No Drawings

PROCESS FOR PRODUCING PYRROLIDINE DERIVATIVE AND SALT THEREOF

TECHNICAL FIELD

The present invention relates to an industrial process for producing pyrrolidine derivative or a salt thereof represented by the following general formula (I):

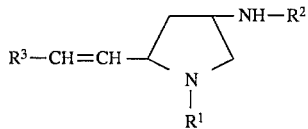
(I)

wherein
$R^1$ is heterocyclic(lower)alkyl,
$R^2$ is acyl, and
$R^3$ is carboxy(lower)alkyl or protected carboxy(lower)alkyl, and is applicable in the medical field.

BACKGROUND ART

Pyrrolidine derivatives of the above general formula (I), or salts thereof and a method for producing them are known as disclosed in Japanese Patent Publication No. 2-152960.

DISCLOSURE OF INVENTION

The method described in the above-mentioned bulletin for the production of compounds of general formula (I) is disadvantageous in that it requires a long series of steps complicating the production and provides only a very low overall yield rendering the production cost high.

The object of this invention is to provide an industrially excellent production method for producing compounds of general formula (I) and salts thereof which is superior to the above known production process in simplicity and in yield.

The method for producing said pyrrolidine derivative (I) according to this invention is as follows.

Process (1)

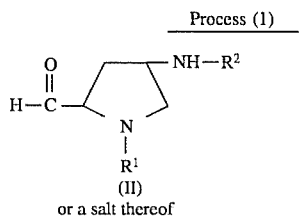
(II)
or a salt thereof

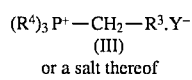
(III)
or a salt thereof

Process (1)
-continued

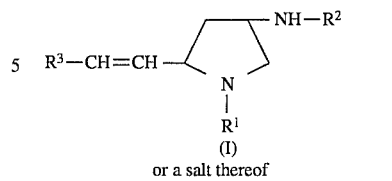
(I)
or a salt thereof wherein $R^1$ $R^2$ and $R^3$ are each as defined above,
$R^4$ is aryl, and
$Y^\ominus$ is an anion.

The starting compound (II) is novel and can be produced by the following processes.

Process (A)

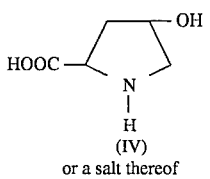
(IV)
or a salt thereof

↓ introduction reaction of the carboxy protective group

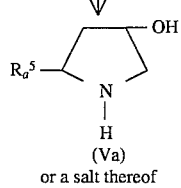
(Va)
or a salt thereof

Process (B)

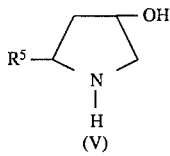
(V)
or a salt thereof

① | $R^1$—$X^1$
(VI)
or a salt thereof

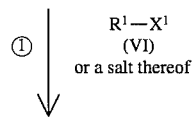

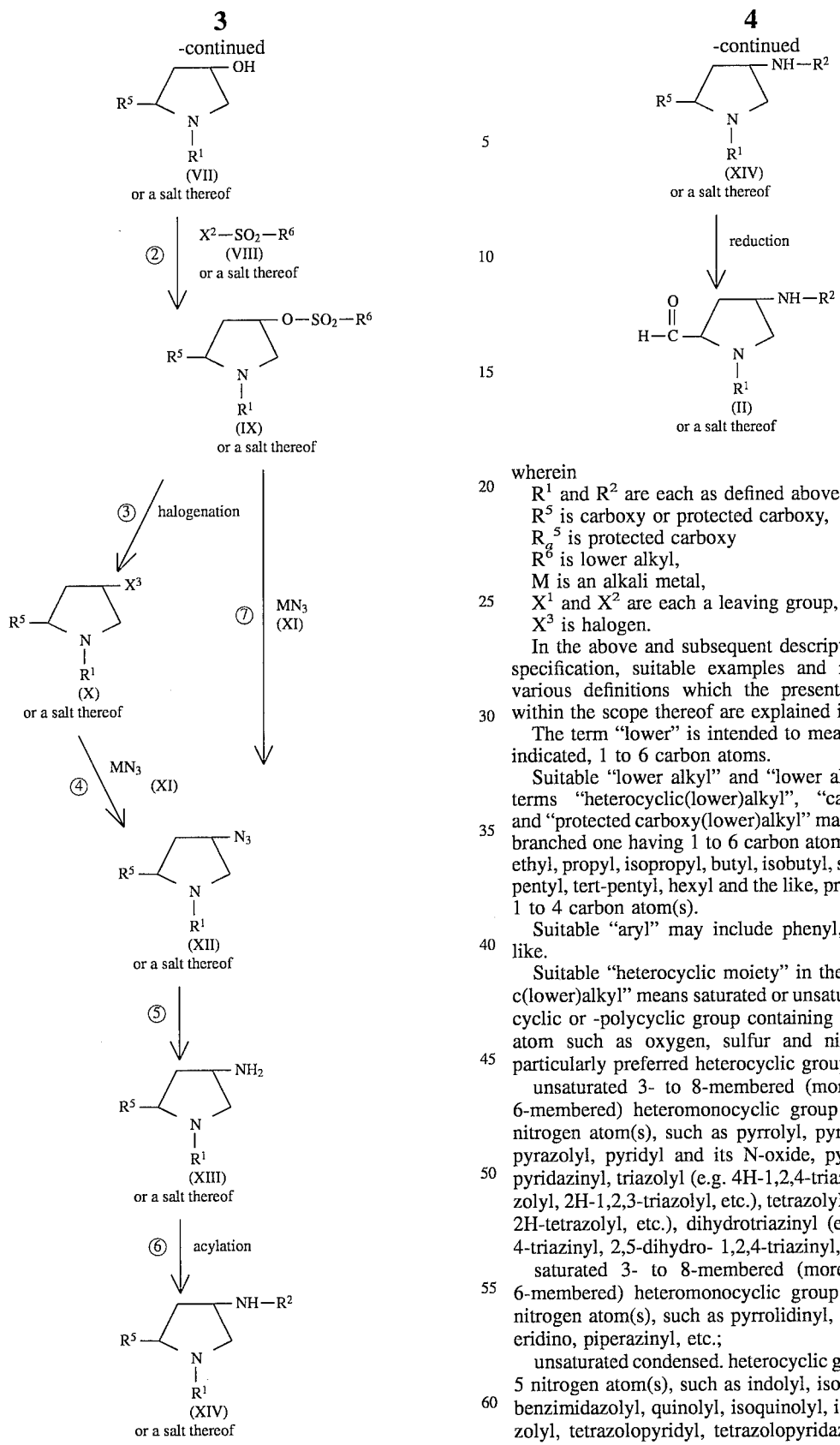

wherein
R¹ and R² are each as defined above,
R⁵ is carboxy or protected carboxy,
$R_a^5$ is protected carboxy
R⁶ is lower alkyl,
M is an alkali metal,
X¹ and X² are each a leaving group, and
X³ is halogen.

In the above and subsequent descriptions of the present specification, suitable examples and illustrations of the various definitions which the present invention include within the scope thereof are explained in detail as follows.

The term "lower" is intended to mean, unless otherwise indicated, 1 to 6 carbon atoms.

Suitable "lower alkyl" and "lower alkyl moiety" in the terms "heterocyclic(lower)alkyl", "carboxy(lower)alkyl" and "protected carboxy(lower)alkyl" may include straight or branched one having 1 to 6 carbon atom(s) such as methyl, ethyl, propyl, isopropyl, butyl, isobutyl, sec-butyl, tert-butyl, pentyl, tert-pentyl, hexyl and the like, preferably one having 1 to 4 carbon atom(s).

Suitable "aryl" may include phenyl, naphthyl, and the like.

Suitable "heterocyclic moiety" in the term "heterocyclic(lower)alkyl" means saturated or unsaturated hetero-monocyclic or -polycyclic group containing at least one heteroatom such as oxygen, sulfur and nitrogen atoms. The particularly preferred heterocyclic group may be unsaturated 3- to 8-membered (more preferably 5- or 6-membered) heteromonocyclic group containing 1 to 4 nitrogen atom(s), such as pyrrolyl, pyrrolinyl, imidazolyl, pyrazolyl, pyridyl and its N-oxide, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g.-4,5-dihydro-1,2, 4-triazinyl, 2,5-dihydro- 1,2,4-triazinyl, etc.), etc.;

saturated 3- to 8-membered (more preferably 5- or 6-membered) heteromonocyclic group containing 1 to 4 nitrogen atom(s), such as pyrrolidinyl, imidazolidinyl, piperidino, piperazinyl, etc.;

unsaturated condensed. heterocyclic group containing 1 to 5 nitrogen atom(s), such as indolyl, isoindolyl, indolizinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl, etc.), dihydrotriazolopyridazinyl, etc.;

unsaturated 3- to 8-membered (more preferably 5- or 6-membered) heteromonocyclic group containing 1 or 2 oxygen atom(s) and 1 to 3 nitrogen atom(s), such as oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3- to 8-membered (more preferably 5- or 6-membered) heteromonocyclic group containing 1 or 2 oxygen atom(s) and 1 to 3 nitrogen atom(s), such as morpholinyl, etc.;

unsaturated condensed heterocyclic group containing 1 or 2 oxygen atom(s) and 1 to 3 nitrogen atom(s), such as benzoxazolyl, benzoxadiazolyl, etc.;

unsaturated 3- to 8-membered (more preferably 5- or 6-membered) heteromonocyclic group containing 1 or 2 sulfur atom(s) and 1 to 3 nitrogen atom(s), such as thiazolyl (e.g. 1,2-thiazolyl, etc.), thiazolinyl, thiadiazolyl (e.g. 1,2, 4-thiadiazolyl, 1,3,4-thiadiazolyl, 1,2,5-thiadiazolyl, 1,2,3-thiadiazolyl, etc.), etc.;

saturated 3- to 8-membered (more preferably 5- or 6-membered) heteromonocyclic group containing 1 to 2 sulfur atom(s) and 1 to 3 nitrogen atom(s), such as thiazolidinyl, etc.;

unsaturated 3- to 8-membered (more preferably 5- or 6-membered) heteromonocyclic group containing one sulfur atom, such as thienyl, etc.;

unsaturated 3- to 8-membered (more preferably 5-or 6-membered) heteromonocyclic group containing one oxygen atom, such as furyl, etc.;

unsaturated condensed heterocyclic group containing 1 or 2 sulfur atoms(s) and 1 to 3 nitrogen atom(s), such as benzothiazolyl, benzothiadiazolyl, etc.; and the like.

Suitable "acyl" may include lower alkanoyl such as formyl, acetyl, propionyl, butyryl, isobutyryl, valeryl, isovaleryl, pivaloyl, etc.; lower alkoxycarbonyl such as methoxycarbonyl, ethoxycarbonyl, propoxycarbonyl, isopropoxycarbonyl, butoxycarbonyl, tert-butoxycarbonyl, pentyloxycarbonyl, tert-pentyloxycarbonyl, hexyloxycarbonyl, etc.; lower alkylsulfonyl such as methylsulfonyl, ethylsulfonyl, propylsulfonyl, isopropylsulfonyl, butylsulfonyl, tert-butylsulfonyl, pentylsulfonyl, tert-pentylsulfonyl, hexylsulfonyl, etc.; arylsulfonyl such as phenylsulfonyl, naphthylsulfonyl, etc.; aroyl such as benzoyl, naphthoyl, etc.; ar(lower)alkanoyl, such as phenylacetyl, phenylpropionyl, etc.; cyclo(lower)alkyl(lower)alkanoyl such as cyclohexylacetyl, cyclopentylacetyl, etc.; ar(lower)alkoxycarbonyl such as benzyloxycarbonyl, phenethyloxycarbonyl, etc.; arylcarbamoyl such as phenylcarbamoyl, naphthylcarbamoyl, etc.; heterocyclicsulfonyl such as heteromonocyclic sulfonyl (e.g. thienylsulfonyl, furylsulfonyl, pyridylsulfonyl, etc.), etc.; and the like.

The acyl group mentioned above may be substituted with 1 to 3 suitable substituent(s) such as halogen (e.g. chlorine, bromine, fluorine and iodine), lower alkyl (e.g. methyl, ethyl, propyl, isopropyl, butyl, isobutyl, sec-butyl, tert-butyl, pentyl, tert-pentyl, hexyl, etc.), lower alkoxy (e.g. methoxy, ethoxy, propoxy, isopropoxy, butoxy, tert-butoxy, pentyloxy, tert-pentyloxy, hexyloxy, etc.), nitro, mono-(or di- or tri) halo(lower)alkyl (e.g. chloromethyl, bromomethyl, chloropropyl, 1,2-dichloroethyl, 1,2-dibromoethyl, 2,2-dichloroethyl, trifluoromethyl, 1,2,2-trichloroethyl, etc.) or the like.

Suitable "protected carboxy" and "protected carboxy moiety" in the term "protected carboxy(lower)alkyl" may include carbamoyl; acylcarbamoyl such as lower alkylsulfonylcarbamoyl (e.g. methylsulfonylcarbamoyl, ethylsulfonylcarbamoyl, propylsulfonylcarbamoyl, isopropylsulfonylcarbamoyl, butylsulfonylcarbamoyl, tert-butylsulfonylcarbamoyl, pentylsulfonylcarbamoyl, tert-pentylsulfonylcarbamoyl, hexylsulfonylcarbamoyl, etc.), arylsulfonylcarbamoyl (e.g. phenylsulfonylcarbamoyl, naphthylsulfonylcarbamoyl, etc.) or the like; esterified carboxy in which said ester may be the ones such as lower alkyl ester (e.g. methyl ester, ethyl ester, propyl ester, isopropyl ester, butyl ester, isobutyl ester, tert-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), mono-(or di or tri)halo(lower) alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.), lower alkylsulfonyl(lower)alkyl ester (e.g. mesylmethyl ester, 2-mesylethyl ester, etc.), ar(lower)alkyl ester such as phenyl(lower)alkyl ester which may be substituted by one or more suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-tert-butylbenzyl ester, etc. or the like, lower alkoxycarbonyloxy(lower)alkyl ester (e.g. methoxycarbonyloxymethyl ester, ethoxycarbonyloxymethyl ester, ethoxycarbonyloxyethyl ester, etc.), aroyloxy(lower)alkyl ester (e.g. benzoyloxymethyl ester, benzoyloxyethyl ester, toluoyloxyethyl ester, etc.), aryl ester which may have one or more suitable substituent(s) (e.g. phenyl ester, tolyl ester, tert-butylphenyl ester, xylyl ester, mesityl ester, cumenyl ester, etc.), and the like.

Suitable "halogen" may include chlorine, bromine, fluorine and iodine.

Suitable "leaving group" may include acid residue and the like, and the suitable examples thereof are halogen (e.g. chlorine, bromine, fluorine, etc.), sulfonyloxy (e.g. methylsulfonyloxy, phenylsulfonyloxy, etc.), and the like.

Suitable "anion" may include halide ion (e.g. chloride ion, bromide ion, fluoride ion, etc.), and the like.

Suitable "alkali metal" may include sodium, potassium, and the like.

Suitable pharmaceutically acceptable salts of the object compound (I) are conventional nontoxic salts and include a metal salt such as an alkali metal salt (e.g. sodium salt, potassium salt, etc.) and alkaline earth metal salt (e.g. calcium salt, magnesium salt, etc.), ammonium salt an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, lysine, etc.), and the like.

The followings are the preferred examples of compound (I).

$R^1$ is unsaturated 5- or 6-membered heteromonocyclic(lower)alkyl containing 1 to 4 nitrogen atom(s) [more preferably pyridyl(lower)alkyl; most preferably pyridyl($C_1$-$C_4$)alkyl];

$R^2$ is arylsulfonyl which may have 1 to 3 substituent(s) selected from the group consisting of halogen, lower alkyl, lower alkoxy and mono(or di or tri)halo(lower)alkyl [more preferably phenylsulfonyl which may have 1 or 2 substituent(s) selected from the group consisting of halogen, lower alkyl, lower alkoxy and mono(or di or tri)halo(lower)alkyl; most preferably phenylsulfonyl which may have halogen], $R^3$ is carboxy(lower)alkyl or protected carboxy(lower) alkyl [more preferably esterified carboxy(lower)alkyl; most preferably lower alkoxycarbonyl(lower)alkyl].

The processes for preparing the object compound (I) and starting compound (II) of the present invention are explained in detail in the following.

Process (1)

The compound (I) or a salt thereof can be produced by reacting the compound (II) or a salt thereof with the compound (III) or a salt thereof.

The reaction is generally carried out in the common solvent, such as acetone, dioxane, acetonitrile, chloroform, methylene chloride, ethylene chloride, tetrahydrofuran, ethyl acetate, N,N-dimethylformamide, dimethyl sulfoxide or any other solvent that does not interfere with the reaction.

While the reaction temperature is not critical, this reaction is generally conducted under cooling to warming.

This reaction is preferably conducted in the presence of an inorganic base such as alkali metal hydroxide (e.g. sodium hydroxide, potassium hydroxide, etc.), alkaline earth metal hydroxide (e.g. magnesium hydroxide, potassium hydroxide, etc.), alkali metal carbonate (e.g. sodium carbonate, potassium carbonate, cesium carbonate, etc.), alkaline earth metal carbonate (e.g. magnesium carbonate, calcium carbonate, etc.), alkali metal hydrogencarbonate (e.g. sodium hydrogencarbonate, potassium hydrogencarbonate, etc.), alkali metal acetate (e.g. sodium acetate, potassium acetate, etc.), alkaline earth metal phosphate (e.g. magnesium phosphate, calcium phosphate, etc.), alkali metal hydrogenphosphate (e.g. disodium hydrogenphosphate, dipotassium hydrogenphosphate, etc.), alkali metal hydride (e.g. sodium hydride etc.), alkali metal (lower)alkoxide (e.g. sodium methoxide, sodium ethoxide, potassium methoxide, potassium ethoxide, potassium t-butoxide, etc.) and the like, or an organic base such as tri(lower)alkylamine (e.g. trimethylamine, triethylamine, diisopropylethylamine, etc.), pyridine, lutidine, picoline, dimethylaminopyridine, N-(lower)alkylmorpholine and the like (preferably in the presence of an organic base).

Process (A)

The compound (Va) or a salt thereof can be produced by subjecting the compound (IV) or a salt thereof to introduction reaction of the carboxy protective group.

This reaction can be carried out by the procedure described in Preparation 1 or similar manners thereto.

Process (B)-①

The compound (VII) or a salt thereof can be produced by reacting the compound (V) or a salt thereof with the compound (VI) or a salt thereof.

The reaction is generally conducted in the common solvent, such as acetone, dioxane, chloroform, methylene chloride, ethylene chloride, tetrahydrofuran, ethyl acetate, N,N-dimethylformamide, dimethylsulfoxide or any other solvent that does not interfere with the reaction.

While the reaction temperature is not critical, this reaction is generally carried out under cooling, at room temperature, under warming or heating.

Process (B)-②

The compound (IX) or a alt thereof can be produced by reacting the compound (VII) or a salt thereof with the compound (VIII) or a salt thereof.

This reaction is generally conducted in the common solvent such as dichloromethane, chloroform, methylene chloride, ethylene chloride, tetrahydrofuran, N,N-dimethylformamide or any other solvent that does not interfere with the reaction.

While the reaction temperature is not critical this reaction is generally conducted under cooling or at room temperature.

This reaction is preferably conducted in the presence of an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, cesium carbonate, etc.), alkaline earth metal carbonate (e.g. magnesium carbonate, calcium carbonate, etc.), alkali metal hydrogencarbonate (e.g. sodium hydrogencarbonate, potassium hydrogencarbonate, etc.), alkali metal acetate (e.g. sodium acetate, potassium acetate, etc.), alkaline earth metal phosphate (e.g. magnesium phosphate, calcium phosphate, etc.), alkali metal hydrogenphosphate (e.g. disodium hydrogenphosphate, dipotassium hydrogenphosphate, etc.) and the like, or an organic base such as trialkylamine (e.g. trimethylamine, triethylamine etc..) and the like.

Process (B)-③

The compound (X) or a salt thereof can be produced by subjecting the compound (IX) or a salt thereof to halogenation reaction.

This reaction can be carried out by the procedure described in Preparation 3 or similar manners thereto.

It should be noted that this reaction reverses the configuration of the substituent in 4-position of the pyrrolidine ring.

Process (B)-④

The compound (XII) or a salt thereof can be produced by reacting the compound (X) or a salt thereof with the compound (XI).

This reaction is generally carried out in the common solvent such as dimethyl sulfoxide or any other solvent that does not interfere with the reaction.

The reaction temperature is not critical but the reaction is generally carried out under warming or under heating. This reaction reverses the configuration of the substituent in 4-position of the pyrrolidine ring.

Process (B)-⑤

The compound (XIII) or a salt thereof can be produced by subjecting the compound (XII) or a salt thereof to hydrogenation reaction.

This reaction can be conducted by the procedure described in Preparation 5 or similar manners thereto.

Process (B)-⑥

The compound (XIV) or a salt thereof can be produced by reacting the compound (XIII) or a salt thereof with an acylating agent.

The acylating agent is an organic acid, i.e. $R^2$-OH (wherein $R^2$ is an acyl group), or its reactive derivative or a salt thereof. The preferred examples of said reactive derivative of organic acid includes the derivatives commonly employed, such as the acid halide (e.g. acid chloride, acid bromide, etc.), acid azide, acid anhydride, activated amide, activated ester, isocyanate, for example, an aryl isocyanate (e.g. phenyl isocyanate, etc.), and the like.

When the free acid is used as the acylating agent, the acylation reaction is preferably conducted in the presence of the conventional condensing agent such as N,N'-dicyclohexylcarbodiimide, etc.

The reaction is preferably carried out in the presence of an inorganic or organic base such as those mentioned for process (B)-②.

This reaction is generally conducted in a solvent which does not interfere with the reaction, such as water, methanol, ethanol, propanol, dichloromethane, tetrahydrofuran, chloroform, ethyl acetate and the like.

The reaction temperature is not critical and the reaction can be carried out under cooling to heating.

Process (B)-⑦

The compound (XII) or a salt thereof can be produced by reacting the compound (IX) or a salt thereof with the compound(XI).

This reaction can be carried out in the same manner to that of Process B-④ and, therefore, the reaction conditions can be referred to those of the Process (B)-④.

It should be noted that this reaction reverses the configuration of the substituent in 4-position of the pyrrolidine ring.
Process (C)

The compound (II) or a salt thereof can be produced by subjecting the compound (XIV) or a salt thereof to reduction reaction.

This reduction reaction is generally carried out using a reducing agent such as di(lower)alkylaluminum hydride (e.g. diisobutylaluminum hydride, etc.), an alkali metal aluminum hydride (e.g. lithium aluminum hydride, sodium aluminum hydride, potassium aluminum hydride etc.), and the like.

This reaction is generally conducted in the common solvent such as methylene chloride, chloroform, toluene, tetrahydrofuran, or any other solvent that does not interfere with the reaction.

The reaction temperature is not critical and the reaction is generally carried out under cooling or at room temperature.

The object compound (I) of this invention and pharmaceutically acceptable salts thereof are thromboxane $A_2$ ($TXA_2$) antagonists and $TXA_2$ synthetase inhibitors and, therefore, they are useful for the prophylaxis and/or therapy of thrombotic diseases (for example, transient cerebral ischemic attack, cerebral apoplexy, unstable angina, myocardial infarction, peripheral circulatory insufficiency, thrombus formation after percutaneous transluminal coronary angioplasty, disseminated intravascular coagulation syndrome, etc.), allergic diseases (e.g. asthma, etc.), nephritis, peptic ulcer, hemicrania, diabetic neuropathy, diabetic angiopathy, restenosis after percutaneous transluminal coronary angioplasty, adult respiratory distress syndrome, shock, hepatic disorders (e.g. hepatitis, etc.), cerebral vasospasm after subarachnoidal hemorrhage, hypertension, arteriosclerosis, cancerous metastasis, thrombus formation on extracorporeal circulation, thrombus formation on transplantation, conjunctivitis, etc. and for reducing nephrotoxicity induced by immunosuppressant drugs such as cyclosporin at renal transplantation, and can be also used with fibrinolytic agents in order to increase the effect of fibrinolytic agents.

Furthermore, compound (I) and pharmaceutically acceptable salts thereof are useful for the prophylaxis and/or therapy of cerebral infarction such as acute cerebral infarction, arrhythmia, angina pectoris and so The following test examples indicate that Compound (I) and pharmaceutically acceptable salts thereof are useful for the prophylaxis and/or therapy of cerebral infarction, arrhythmia, angina pectoris and so on.
Test compound (2S, 4R)-2-[(Z)-5-Carboxy-1-pentenyl]-4-(4-chloro-phenylsulfonylamino)-1-(3-pyridylmethyl) pyrrolidine hydrochloride (hereinafter referred to briefly as test compound (I)).

Test Example 1

Effect on the cerebral infarct following ligation of middle cerebral artery in SHR rats Nine-week-old male spontaneously hypertensive rats (SHRs, Charles River Japan Inc.) were used in the test.

After induction of anesthesia with 4% halothane (100% $O_2$) in rats, the middle cerebral artery was occluded with an electric coagulator. Immediately after occlusion, the introduction of halothane was stopped and the incised skin area was sutured. Test compound (I) was suspended in 0.5% methylcellulose solution and the suspension was administered orally in a dosing volume of 5 ml/kg immediately after artery occlusion.

Twenty-four hours after occlusion of the middle cerebral artery, the brain was removed from the rat and after the bregma was located, a coronary section 2 mm posterior to the bregma was prepared. This section was immersed in 2% triphenyltetrazolium chloride (TTC) solution and maintained at 37° C. for 40 minutes. After staining, the cerebral section was photographed and the area ratio of the infarct to the hemisphere (%) was calculated for each cut surface using a computerized analyzer.

For statistical analysis, the Mann-Whitney U-test was used.

|  | Dose (mg/kg) | Number of animals | Item | Results |
|---|---|---|---|---|
| Control group | 0 | 7 | Non-infarcted area (mm$^2$) | 43.167 ± 1.253 |
|  |  |  | Area of cortical infarct (mm$^2$) | 12.116 ± 1.302 |
|  |  |  | Total area (mm$^2$) | 55.283 ± 1.217 |
|  |  |  | % Infarct | 21.823 ± 2.194 |
| Drug-treated group | 320 | 9 | Non-infarcted area (mm$^2$) | **49.299 ± 1.301 |
|  |  |  | Area of cortical infarct (mm$^2$) | 9.103 ± 0.491 |
|  |  |  | Total area (mm$^2$) | 58.402 ± 1.203 |
|  |  |  | % Infarct | *15,643 ± 0.392 |

Mean ± SE
**$p < 0.01$ compared with control
*$p < 0.05$ compared with control

Test Example 2

Effect on arrhythmia following coronary ischemia-reperfusion in rats

Male Wistar rats (11 weeks old) fasted for 24 hours were anesthetized with pentobarbital Na, 50 mg/kg i.p. After thoracotomy under artificial respiration, the descending branch of the coronary artery was compressed by suction to arrest the blood flow. After 5 minutes perfusion was reestablished and the animals were observed for ventricular fibrillation (VF) and death for 5 minutes.

Test compound (I) was administered orally 1 hour before arrest of blood flow.

|  | Dose (mg/kg) | Number of animals | Incidence of VF (%) | Mortality rate (%) |
|---|---|---|---|---|
| Control group | — | 17 | 94.1 | 52.9 |
| Drug-treated group | 100 | 6 | 50* | 0* |

*$p < 0.05$ compared with control

Test Example 3

Effect on vasopressin-induced angina in angina model rats

Mole Donryu rats (6 weeks old) fasted for 24 hours were anesthetized with pentobarbital Na, 60 mg/kg i.p. Then, each animal was fixed in supine position and needle electrodes for ECG were affixed to the four limbs. ECG was recorded in Lead II. Vasopressin (Sigma), 0.21 U/kg, was administered into the femoral vein and ECG changes were recorded.

The onset of angina was assessed by a depression of ST segment ($\Delta$ST ($\mu$V)).

Test compound (I) was administered orally 1 hour before vasopressin administration.

|  | Dose (mg/kg) | Number of animals | $\Delta$ ST ($\mu$V) |
|---|---|---|---|
| Control group | — | 7 | 136 ± 13 |
| Drug-treated group | 320 | 8 | 62 ± 26 |

Mean ± SE

The object compound (I) or a pharmaceutically acceptable salt thereof can usually be administered to mammals including human being, generally in the form of a conventional pharmaceutical composition such as capsule, micro-capsule, tablet, granule, powder, troche, syrup, aerosol, inhalation, solution, injection, eye-drop, nasal drop, suspension, emulsion, suppository, ointment, or the like.

The pharmaceutical composition of this invention may contain a various organic and/or inorganic carrier substances which are commonly used in pharmaceutical preparations such as excipient (e.g. sucrose, starch, mannit, sorbit, lactose, glucose, cellulose, talc, calcium phosphate, calcium carbonate, etc.), binding agent (e.g. cellulose, methylcellulose, hydroxypropylcellulose, polypropylpyrrolidone, gelatin, gum arabic, polyethylene glycol, sucrose, starch, etc.), disintegrating agent (e.g. starch, carboxymethylcellulose, calcium carboxymethylcellulose, hydroxypropylstarch, glycol-starch sodium, sodium hydrogencarbonate, calcium phosphate, calcium citrate, etc.), lubricant (e.g. magnesium stearate, talc, sodium lauryl sulfate, etc.), flavoring agent (e.g. citric acid, menthol, glycine, orange powder, etc.), preservative (e.g. sodium benzoate, sodium hydrogen sulfite, methylparaben, propylparaben, etc.), stabilizer (e.g. citric acid, sodium citrate, acetic acid, etc.), suspending agent (e.g. methylcellulose, polyvinylpyrrolidone, aluminum stearate, etc.), dispersing agent, aqueous diluting agent (e.g. water, etc.), base wax (e.g. cacao butter, polyethylene glycol, white petrolatum, etc.) and the like.

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given for the purpose of illustrating the present invention in more detail.

Preparation 1

In an atmosphere of nitrogen, (2S,4R)-2-carboxy-4-hydroxypyrrolidine (100 g, 0.763 mol) was suspended in methanol (400 ml) and the suspension was cooled to 5°–10° C. Then, thionyl chloride (99.8 g, 0.839 mol) was added dropwise thereto under 20° C. After completion of the dropwise addition, the reaction mixture was warmed to 60°–62° C. and stirred at this temperature for 1 hour. The reaction mixture was then cooled to 25°–30° C. for crystallization. To the mixture was added diisopropyl ether (180 ml) dropwise. After completion of the dropwise addition, the mixture was cooled to 0°–5° C. and stirred for 1 hour. The resulting crystal was collected by filtration and washed with diisopropyl ether (200 ml) twice. The washed crystal was dried in vacuo overnight to provide (2S,4R)-2-methoxycarbonyl-4-hydroxypyrrolidine hydrochloride (134.8 g).

IR (Nujol): 3320, 1740, 1590, 1080, 1620, 900 cm$^{-1}$

NMR (DMSO-d$_6$, $\delta$): 5.64 (1H, s), 4.50-4.40 (1H, m), 4.42 (1H, s), 3.70 (1H, d, J=12 Hz), 3.60 (1H, d, J=12 Hz), 3.07 (1H, d, J=12 Hz), 2.22-2.20 (1H, m)

Preparation 2

In an atmosphere of nitrogen, 3-hydroxymethylpyridine (35.95 g, 0.329 mol) was dissolved in N,N-dimethylformamide (250 ml) followed by cooling to −15°−−20° C. Then, triethylamine (36.65 g, 0.329 mol) was added thereto and methanesulfonyl chloride (41.45 g, 0.362 mol) was added dropwise to the mixture at 0°−−10° C. After completion of the dropwise addition, the mixture was stirred at −10° C. for 30 minutes. To this mixture were added (2S,4R)-2-methoxycarbonyl-4-hydroxypyrrolidine hydrochloride (50 g, 0.275 mol) and triethylamine (100 g, 0.988 mol) followed by warming to 65° C. The mixture was stirred at 65° C. for 1 hour to provide a reaction mixture containing (2S,4R)-1-(3-pyridylmethyl)-2-methoxycarbonyl- 4-hydroxypyrrolidine. This reaction mixture was cooled to −20° C. and triethylamine (66.8 g, 0.66 mol) was added thereto. Then, methanesulfonyl chloride (75.6 g, 0.66 mol) was added thereto dropwise at −20°−−15° C. The mixture was stirred at −20°−−25° C. for 1 hour, after which it was poured into ethyl acetate (1 l)-water (1 l) and extracted. After phase separation, the aqueous layer was extracted with ethyl acetate (500 ml) twice. The ethyl acetate layer was combined and washed with a saturated aqueous sodium chloride solution (125 ml). The ethyl acetate layer was concentrated to dryness under reduced pressure to provide (2S,4R)-1-(3-pyridylmethyl)-2-methoxycarbonyl-4-methylsulfonyloxypyrrolidine (84.65 g) as an oil.

NMR (CD$_3$OD, $\delta$): 9.8-9.6 (2H, m), 8.2-8.0 (1H, m), 7.6 (1H, m), 5.25 (1H, q, J=3.6 Hz), 4.19, 4.08, 3.86, 3.75 (2H, ABq), 3.68 (3H, s), 3.42 (1H, dd, J=5.8 Hz, J=12 Hz), 3.05 (3H, s), 3.00 (1H, s), 2.40–2.55 (2H, m)

Preparation 3

In an atmosphere of nitrogen, (2S,4R)-i-( 3-pyridylmethyl)-2-methoxycarbonyl-4-methylsulfonyloxypyrrolidine (84.65 g) was dissolved in polyethylene glycol-400 (400 ml) followed by addition of lithium chloride (40 g, 0.943 mol). The mixture was warmed to 85°–90° C. and stirred at that temperature for 4–5 hours. The reaction mixture was then cooled to −20°−−25° C. and ethyl acetate (800 ml)-water (400 ml) was added thereto for extraction. After phase separation, the aqueous layer was adjusted to pH 9–9.5 with 24% sodium hydroxide in water (pH prior to adjustment: 4.8) and extracted with ethyl acetate (400 ml) twice. The ethyl acetate layer was combined and washed with a saturated aqueous sodium chloride solution (200 ml). The ethyl acetate solution was then concentrated to dryness under reduced pressure to provide (2S,4S)-1-(3-pyridylmethyl)-2-methoxycarbonyl-4-chloropyrrolidine (60.6 g) as an oil.

NMR (CDCl$_3$, δ): 8.55 (2H, m), 7.50 (1H, m), 7.30 (1H, m), 4.20 (1H, m), 4.00–4.15 (2H, m), 3.73 (3H, s), 3.75 (1H, m), 3.30 (1H, m), 3.05 (1H, m), 2.95 (1H, m), 2.20 (1H, m)

Preparation 4

In an atmosphere of nitrogen,(2S,4S)-1-( 3-pyridylmethyl)-2-methoxycarbonyl-4-chloropyrrolidine (60.6 g) was dissolved in dimethyl sulfoxide (600 ml) followed by addition of sodium azide (60 g, 0.923 mol) and the mixture was warmed to 85°–90° C. and stirred at the same temperature for 5–6 hours. The reaction mixture was cooled to 40°–50° C. and poured into ethyl acetate (1 l)-water (1 l) for extraction. After phase separation, the aqueous layer was re-extracted with ethyl acetate (500 ml). The ethyl acetate layer was combined and washed with a saturated aqueous sodium chloride solution (250 ml). The ethyl acetate solution was concentrated to dryness under reduced pressure to provide (2S,4R)-1-( 3-pyridylmethyl)-2-methoxycarbonyl-4-azidopyrrolidine (49.4 g) as an oil.

NMR (CDCl$_3$, δ): 8.55 (2H, m), 7.70 (1H, m), 7.26 (1H, m), 4.10 (1H, m), 3.97, 3.90, 3.71, 3.64 (2H, ABq), 3.68 (3H, s), 3.35 (1H, m), 2.60 (1H, m), 2.00–2.40 (2H, m)

Preparation 5

In an atmosphere of nitrogen,(2S,4R)-1-( 3-pyridylmethyl)-2-methoxycarbonyl-4-azidopyrrolidine (49.4 g) was dissolved in ethyl acetate (500 ml) followed by addition of triphenylphosphine (60.75 g, 0.232 mol) at 20°–30° C. (foaming took place). After completion of addition, the mixture was warmed to 40°–45° C. and stirred for 30 minutes. The mixture was diluted with water (16.5 ml) and warmed and stirred at 60°–65° C. for 1.5 hours to provide a reaction mixture containing (2S,4R)-1-(3-pyridylmethyl)-2-methoxycarbonyl-4-aminopyrrolidine. This reaction mixture was cooled to 5°–10° C. and adjusted to pH 3.5 with 1N hydrochloric acid (ca. 350 ml). After phase separation, the organic layer was washed with 1% hydrochloric acid (125 ml). The aqueous layer was combined and adjusted to pH 7.0 with triethylamine (ca. 20 ml) (pH prior to adjustment:1.5). This aqueous solution was cooled to 5° C. and ethyl acetate (475 ml) and triethylamine (70.5 g, 0.696 mol) were added thereto in that order. Then, at 5°–10° C., 4-chlorobenzenesulfonyl chloride (49 g, 0.232 mol) was added in 3 successive portions and the mixture was stirred at 5° C. for 1 hour. The reaction mixture was adjusted to pH 2.0 with 6N-hydrochloric acid. After phase separation, the organic layer was washed with 1% hydrochloric acid (125 ml). The aqueous layer was combined and adjusted to pH 7.0 with 24% aqueous sodium hydroxide solution. The aqueous solution was extracted with ethyl acetate (500 ml) and the extract was washed with a saturated aqueous sodium chloride solution (125 ml). The ethyl acetate layer was concentrated to 187.5 ml under reduced pressure and the concentrate was stirred at 20°–25° C. for 1.5 hours for crystallization and ripening. To this solution was added diisopropyl ether (562.5 ml) dropwise and the mixture was stirred for 1 hour. The resulting crystal was collected by filtration and washed with diisopropyl ether (100 ml). The washed crystal was dried in vacuo overnight to provide (2S,4R)-1-( 3-pyridylmethyl)-2-methoxycarbonyl-4-(4-chlorophenylsulfonylamino)pyrrolidine (51.51 g) as a crystal.

IR (Nujol): 1740, 1590, 1340, 1160 cm$^{-1}$

NMR (CDCl$_3$, δ): 8.51-8.45 (2H, m), 7.70 (2H, d, J=11.3 Hz), 7.63-7.58 (1H, m), 7.42 (2H, d, J=11.3Hz), 7.28-7.21 (1H, m), 6.30 (1H, d, J=8 Hz), 3.95 (1H, m), 3.85, 3.78, 3.65, 3.58 (2H, ABq), 3.65 (3H, s), 3.50 (1H, m), 3.15 (1H, m), 2.40-2.20 (2H, m), 2.00 (1H, m)

Preparation 6

In an atmosphere of nitrogen, (2S,4R)-1-( 3-pyridylmethyl)-2-methoxycarbonyl-4-(4chlorophenylsulfonylamino)pyrrolidine (10 g, 0.0244 mol) was dissolved in methylene chloride (200 ml) and the solution was cooled to −50°—55° C. Then, 1M diisobutylaluminum hydride in toluene (73.2 ml, 0.0732 mol) was added thereto dropwise at −50° C. and the mixture was stirred for 30 minutes. Then, 20% sodium potassium tartrate solution was added thereto at 25° C. for precipitation of insolubles. The insolubles were separated by filtration and washed with methylene chloride. The mother liquor and the washings were combined and, after phase separation, the methylene chloride layer was taken. The methylene chloride layer was concentrated to dryness to provide (2S,4R)-1-( 3-pyridylmethyl)-2-formyl-4-(4-chlorophenylsulfonylamino)-pyrrolidine (10.4 g) as an oil.

NMR (CDCl$_3$, δ): 9.37 (1H, d, J=2.6 Hz), 8.50 (2H, m), 7.75 (2H, d, J=11.3 Hz), 7.60 (1H, m), 7.20- 7.10 (1H, m), 7.40 (2H, d, J=11.3 Hz), 3.81, 3.74, 3.65, 3.58 (2H, ABq), 3.25 (1H, m), 2.20 (1H, m), 1.90 (1H, m)

Example 1

In an atmosphere of nitrogen, potassium t-butoxide (21.9 g, 0.195 mol) was dissolved in tetrahydrofuran (140 ml) and after the solution was cooled to 0°–5° C., (4carboxybutyl)triphenylphosphonium chloride (43.3 g, 0.0975 mol) was added thereto. The mixture was warmed to 40° C. and stirred for 1 hour. The reaction mixture was cooled to 0°–5° C. and a solution of (2S,4R)-1-(3-pyridylmethyl)- 2-formyl-4-(4-chlorophenylsulfonylamino)pyrrolidine (10.4 g) in tetrahydrofuran (60 ml) was added thereto dropwise. This reaction mixture was stirred at −5~5° C. for 1 hour, after which it was poured into methylene chloride (200 ml) and 1N-hydrochloric acid (400 ml) for extraction. After phase separation, the methylene chloride layer was extracted with 1N-hydrochloric acid (200 ml) twice. The aqueous layer was combined and adjusted to pH 5.5 with 24% sodium hydroxide in water (pH prior to adjustment=0.25–0.3). The aqueous solution was extracted with ethyl acetate (200 ml), while the aqueous layer was re-extracted with ethyl acetate (100 ml). The ethyl acetate layer was combined and concentrated to dryness under reduced pressure to provide an oil. This oil was dissolved in 1N-hydrochloric acid (70 ml)-purified water (35 ml) and the solution was adjusted to pH 2.2 by dropwise addition of 1N-aqueous sodium hydroxide solution. The mixture was stirred at 20°–25° C. for crystallization and ripening. During this procedure, 1N-aqueous sodium hydroxide solution was added thereto dropwise so as to maintain the solution at pH 2.2. After (about 1 hour of) ripening, 1N-aqueous sodium hydroxide solution was added thereto dropwise so as to adjust the solution to pH 3.5. The solution was then cooled to 5° C. and stirred for 1 hour. The resulting crystal was collected by filtration, washed with cold purified water (10 ml) and dried in vacuo overnight to provide (2S,4R)-2-[(Z)-5-carboxy-l-pentenyl]- 4-(4-chlorophenylsulfonylamino)-1-(3pyridylmethyl)pyrrolidine hydrochloride (8.0 g) as crude crystal.

IR (Nujol): 3100, 1700, 1340, 1180, 1160, 1000 cm$^{-1}$

NMR (DMSO-d$_6$, δ): 12.0 (1H, br s), 8.85 (3H, m), 8.05 (1H, m), 7.85 (2H, d, J=8.8 Hz), 7.70 (2H, d, J=8.8 Hz), 7.50

(1H, m), 5.70 (2H, m), 4.60 (1H, m), 4.30 (2H, m), 3.95 (1H, m), 3.35 (1H, m), 2.90 (1H, m), 2.30-1.80 (6H, m), 1.60 (2H, m)

Example 2

In 1N-hydrochloric acid (44 ml)-purified water (16 ml) was dissolved crude crystal of (2S,4R)-2-[(Z)- 5-carboxy-1-pentenyl]-4-(4-chlorophenylsulfonylamino)-1-(3-pyridylmethyl)pyrrolidine hydrochloride (8.0 g, 0.016 mol) followed by addition of activated carbon (0.8 g) and the mixture was stirred at 25° C. for 1 hour. Then, clarification-filtration was carried out using a 0.25μ membrane prefilter and the filtrate was washed with 1N-hydrochloric acid (4 ml)-purified water (8 ml). While the filtrate was stirred, 1N-aqueous sodium hydroxide solution was added dropwise so as to adjust the solution to pH 2.0 (pH prior to adjustment:0.4). The mixture was stirred at 20°-25° C. for crystallization and ripening (about 1 hour, pH decreases to 1.51). Then, 1N-aqueous sodium hydroxide solution was added thereto dropwise so as to adjust the solution to pH 2.20. The solution was cooled to 5° C. and 1N aqueous sodium hydroxide solution was added thereto dropwise so as to maintain the solution at pH 2.20. The solution was cooled to 5° C. and 1N-aqueous sodium hydroxide solution was added thereto dropwise so as to maintain the solution at pH 2.20. The solution was then allowed to stand at 0°-5° C. overnight. The next morning the crystal was collected by filtration and washed with cold purified water (8 ml). The washed crystal was dried in vacuo overnight to provide pure crystal (6.77 g) of (2S,4R)- 2-[(Z)-5-carboxy-1-pentenyl]-4-(4-chlorophenylsulfonylamino)-1-(3-pyridylmethyl)pyrrolidine hydrochloride.

We claim:

1. A process of using a compound of the formula:

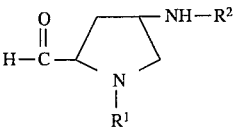

wherein $R^1$ is unsaturated 5-or 6-membered heteromonocyclic(lower)alkyl containing 1 to 4 nitrogen atom(s) and $R^2$ is acyl;

or a salt thereof, which comprises reacting said compound with a compound of the formula:

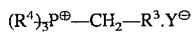

wherein $R^3$ is carboxy(lower)alkyl or protected carboxy(lower)alkyl;

$R^4$ is aryl; and $Y^\ominus$ is an anion; or a salt thereof, to produce a compound of the formula:

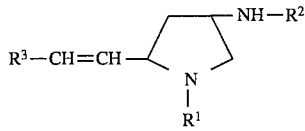

wherein $R^1$, $R^2$ and $R^3$ are each as defined above, or a salt thereof.

* * * * *